(12) United States Patent
Hann

(10) Patent No.: US 9,135,804 B2
(45) Date of Patent: Sep. 15, 2015

(54) SYSTEMS AND METHODS FOR ASSESSING RISKS OF PRESSURE ULCERS

(71) Applicant: Elly Hann, La Jolla, CA (US)

(72) Inventor: Elly Hann, La Jolla, CA (US)

(73) Assignee: PERSIMMON SCIENTIFIC, INC., San Diego, CA (US)

( * ) Notice: Subject to any disclaimer, the term of this patent is extended or adjusted under 35 U.S.C. 154(b) by 111 days.

(21) Appl. No.: 13/786,975

(22) Filed: Mar. 6, 2013

(65) Prior Publication Data
US 2013/0249695 A1 Sep. 26, 2013

Related U.S. Application Data

(60) Provisional application No. 61/614,978, filed on Mar. 23, 2012.

(51) Int. Cl.
| G08B 23/00 | (2006.01) |
| G08B 21/04 | (2006.01) |
| A61B 5/103 | (2006.01) |
| G06Q 10/06 | (2012.01) |
| G06Q 50/22 | (2012.01) |
| A61B 5/00 | (2006.01) |

(52) U.S. Cl.
CPC .......... *G08B 21/0438* (2013.01); *A61B 5/0022* (2013.01); *A61B 5/103* (2013.01); *A61B 5/441* (2013.01); *A61B 5/445* (2013.01); *A61B 5/4842* (2013.01); *A61B 5/7275* (2013.01); *G06Q 10/06311* (2013.01); *G06Q 50/22* (2013.01)

(58) Field of Classification Search
CPC ........ A61B 5/103; A61B 5/6894; A61B 5/11; A61B 5/441; G06Q 50/22; G06Q 10/06311; G08B 21/0438

USPC ........................................................ 340/573.7
See application file for complete search history.

(56) References Cited

U.S. PATENT DOCUMENTS

| 8,321,241 | B1 * | 11/2012 | Mansour et al. ................... 705/3 |
| 8,510,126 | B2 * | 8/2013 | Martin et al. ..................... 705/2 |
| 8,844,073 | B2 * | 9/2014 | Riley et al. ...................... 5/424 |
| 2004/0059199 | A1 * | 3/2004 | Thomas et al. ............... 600/300 |
| 2005/0165284 | A1 * | 7/2005 | Gefen ............................ 600/300 |
| 2005/0222870 | A1 * | 10/2005 | Schumann et al. ............... 705/2 |
| 2005/0224083 | A1 * | 10/2005 | Crass et al. ................... 128/897 |
| 2007/0004971 | A1 * | 1/2007 | Riley et al. .................... 600/300 |
| 2007/0185391 | A1 * | 8/2007 | Morgan ......................... 600/301 |
| 2008/0228526 | A1 * | 9/2008 | Locke et al. ...................... 705/3 |
| 2009/0099480 | A1 * | 4/2009 | Salgo et al. ................... 600/595 |
| 2009/0292558 | A1 * | 11/2009 | Kramer et al. ..................... 705/3 |
| 2010/0106524 | A1 * | 4/2010 | Wu et al. ........................... 705/3 |
| 2010/0312076 | A1 * | 12/2010 | Bly et al. ....................... 600/301 |
| 2011/0191115 | A1 * | 8/2011 | Zalam .............................. 705/2 |
| 2011/0263950 | A1 * | 10/2011 | Larson et al. ................. 600/301 |
| 2011/0313789 | A1 * | 12/2011 | Kamen et al. ..................... 705/3 |

(Continued)

*Primary Examiner* — Quang D Pham
(74) *Attorney, Agent, or Firm* — Carlos R. Villamar; The Villamar Firm PLLC

(57) ABSTRACT

A system, method and computer program product for assessing a risk of developing pressure ulcers, including a user input unit configured to receive facility setting information and objective and subjective information of a patient for a plurality of categories of patient data; a correlation unit configured to determine a corresponding risk value of developing a pressure ulcer for each category of patient data, based on the patient data received in each category; and a risk determination unit configured to determine a level of risk of a patient developing a pressure ulcer based on the correlated risk values.

12 Claims, 12 Drawing Sheets

(56) References Cited

U.S. PATENT DOCUMENTS

| | | | |
|---|---|---|---|
| 2012/0006151 A1* | 1/2012 | DeDe et al. | 74/606 R |
| 2012/0116251 A1* | 5/2012 | Ben-Shalom et al. | 600/587 |
| 2012/0119912 A1* | 5/2012 | Ortega et al. | 340/573.5 |
| 2013/0085777 A1* | 4/2013 | Scheurich et al. | 705/3 |
| 2013/0090571 A1* | 4/2013 | Nourani et al. | 600/587 |
| 2013/0317393 A1* | 11/2013 | Weiss et al. | 600/587 |
| 2013/0346105 A1* | 12/2013 | Ryan et al. | 705/3 |

* cited by examiner

Pressure Ulcer Risk Calculator
A Companion Tool

User: Carol Home Nurse
Patient: Road R Runner
MRN: Spinal Cord Injury
Floor: -
Home Care & Hospice « Back to Home     Logout 1. Age [26]
2. Sex ● Male ○ Female
3. Height [7 ▼] Ft. [9 ▼] Inches
4. Weight (lbs) [160]
5. Unintended weight loss [≥ 10% Weight Lo ▼]  202
6. Diagnosis
 [Immunosuppression
  Kidney Disease (Re
  Liver Disease (Hepa
  Malignancy
  Neuromuscular Dise
  Peripheral Vascular Disease
  Post-op
  Pulmonary Disease
  Spinal Cord Injury
  Sore Sites to Spine]  206
 ← 204

7. Previous Pressure Ulcers (pressure sores) [Yes (Any stage) ▼]  208
8. Any Presence of Pressure Ulcers On Examination [Stage 1 ▼]  210
9. Mobility [Bedfast ▼]
10. Fecal Incontinence ○ Yes ● N  212
11. Braden Scale [Not Available ▼]
13. Lab Values [Not Available ▼]

Height Conversion
Inches ◆ Meters [ ] [Convert]

Weight Conversion
Pounds ◆ Kgs [ ] [Convert]

To view results: ▲ click here

TRENDING  214

|  | Jan | Feb | Mar |
|---|---|---|---|
| Total Number of Patients Under Care | 325 | 350 | 350 |
| Number of Patients at Risk for PU | 20 | 25 | 30 |
| Pressure Ulcer Risk Assessment documented 504 | 20 | 25 | 25 |
| % Assessment within 24 hours | 100% | 100% | 100% |
| Pressure Ulcer Prevention in use | 20 | 25 | 25 |
| Patient/Caregiver education 506 | 20 | 25 | 25 |
| % PU prevention education provided 508 | 100% | 100% | 83% |
| No. patients with PUs on admission 510 | 20 | 20 | 25 |
| Average stage of PU on admission 512 | Stage III | Stage II | Stage II |
| No. patients with agency-acquired PUs 514 | 12 |  |  |
| Average stage of agency-acquired PU 516 | Stage II | Stage II | Stage II |
| Prevalence of PU in the agency 518 | 10% | 9.1% | 10% |
| Incidence of PU in the agency 520 | 3.6% | 3.4% | 2.8% |

| | Trend | Jan | Feb | Mar |
|---|---|---|---|---|
| Total No. Patients  604 | 603 ⬆ | 325 | 350 | 350 |
| Patient at Risk  606 | | 20 | 25 | 30 |
| Patients with PU on Admission  608 | | 20 | 20 | 30 |
| Average Stage  610 | | III | II | II |
| Patients with agency caused PUs  612 | 611 ⬇ | 12 | 12 | 30 |
| Prevalence of PU  614 | | 10% | 9.1% | 10% |
| Incidence of PU  616 | | 3.6% | 3.4% | 2.8% |

Risk Assessment Input Page
200

701

702

NDNQI Restraint & Pressure Ulcer Data Collection Form C (As Adapted by Persimmon Scientific)

| Restraint Information | Pressure Ulcer Information | Types Of Prevention Interventions | Number of Pressure Ulcers | Pressure Ulcer Tables |

Patient Name: 9, 50 Male    704

Pressure Ulcer Information

7. Skin Assessment Documented w/in 24 hrs. of admission
- ● Yes
- ○ No
- ○ Pending (admitted w/in last 24 hours)

706

8. Pressure ulcer risk assessment documented w/in 24 hours of admission?
- ○ Yes
- ○ No
- ● Pending (admitted w/in last 24 hours)

707

9. Admission risk assessment scale and score?
- ☑ Braden scale
- ☐ Braden Q scale
- ☐ NSRAS          14
- ☐ Norton scale    Admission Score
- ☐ Other – assessed risk on admission using another scale or other pt. risk/clinical factors

708

10. How long ago was the last pressure ulcer risk assessment performed? (Exclude risk assessment at time of survey)    710
- ○ 0 – 12 hours
- ○ 12 – 24 hours
- ○ 24 – 48 hours
- ○ 48 – 72 hours
- ○ 72 hrs to 1 week 11. Last risk assessment scale & score? (Exclude risk assessment at time of survey)
- ○ Braden scale
- ○ Braden Q scale
- ○ NSRAS
- ○ Norton scale    Last Score
- ○ Other

712

12. Based on last assessment, is patient "at risk for pressure ulcers"?
- ○ Yes – based on risk assessment score, OR
- ○ Yes – based on other pt. risk/clinical factors
- ○ No

714

13. Pressure ulcer prevention in use w/in past 24 hrs for "at risk" patient?
- ● Yes
- ○ No
- ○ Pending (admitted w/in last 24 hrs)

716

700

FIG. 7

SYSTEMS AND METHODS FOR ASSESSING RISKS OF PRESSURE ULCERS

CROSS REFERENCE TO RELATED DOCUMENTS

The present invention is related to U.S. Provisional Patent Application Ser. No. 61/614,978 of Elly HANN, entitled "SYSTEMS AND METHODS FOR ASSESSING RISKS OF PRESSURE ULCERS," filed on Mar. 23, 2012, the entire disclosure of which is hereby incorporated by reference herein.

FIELD OF THE INVENTION

The present invention relates to systems and methods for assessing a risk level of a patient for developing pressure ulcers, and more particularly to methods and systems for identifying knowledge-based risk scores for a plurality of objective patient data and evaluating the risk scores to determine an overall risk level for developing pressure ulcers (e.g., also known as pressure sores), including integrating such risk levels for a user's workflow and continuity of care, as well as measuring nursing outcomes quality indicators, and the like.

BACKGROUND OF THE INVENTION

Pressure ulcers can develop in a person who is bedridden, confined to a wheelchair, suffer from particular illness or skin condition, or otherwise subject to extended periods of immobility. However, current approaches for prevention of pressure sores, including underpads, pressure redistribution surfaces, electronic sensors, monitoring systems, and the like, still suffer from discovered problems related to effectiveness, practicality of use, economy, maintenance requirements, and the like.

In view of the foregoing, there is the need for methods and systems to more accurately assess the risks of developing pressure ulcers, provide more cost-effective patient management and prevention. In addition, better tools are needed to address continuity of care of at-risk patients, eliminate patient drop during shift change, simplify obtaining nursing outcomes quality measurements, and the like.

SUMMARY OF THE INVENTION

Embodiments described herein are directed to systems and methods for assessing a risk level of a patient which represents a risk of developing a pressure ulcer. The risk level is determined using individual risk scores provided for a plurality of patient data categories based on correlations in risks of pressure ulcer development with those categories. A user provides input patient data on a plurality of patient health factors, after which pre-determined risk scores for the inputted patient data are identified. The risk scores are then used to determine an overall risk assessment level of the risk of the patient for developing a pressure ulcer. The system and method can include selecting a type of patient care facility in order to adjust the risk scores of the patient data categories based on unique risk categories and scores for each type of facility, such as a home, hospital, nursing home, home health agency, hospice, or long term acute care facility, etc. The system and method can receive patient data from an input device and calculate a risk level for the patient based on the patient data and assigned risk scores, and then outputs the risk level to a user on a display. The system and method can automatically calculate or allow for manual input of re-position time intervals based on patient's health condition or healthcare professional's clinical judgment. The system and method can send pre-timed electronic or manual re-position reminders to an individual user or a group of users. The system and method can present groups of patients according to risk levels on an electronic screen to be viewed by multiple users, improving user's workflow and continuity of care between multiple users. The system and method can export pressure ulcer prevention data to a nursing outcomes registries form, bypassing manual labor necessary to upload to the registries website. The system and method can visually and numerically display a patient's assessed risk levels of a pressure ulcer.

Accordingly, in an exemplary aspect there is provided a system, method, and computer program product for assessing a risk of developing pressure ulcers, including a user input unit configured to receive facility setting information and objective and subjective information of a patient for a plurality of categories of patient data; a correlation unit configured to determine a corresponding risk value of developing a pressure ulcer for each category of patient data, based on the patient data received in each category; and a risk determination unit configured to determine a level of risk of a patient developing a pressure ulcer based on the correlated risk values.

The system, method, and computer program product can include a color-coded visual display configured to display risk levels corresponding to the correlated risk values; a multi-user platform configured to allow viewing of the risk levels for allocation of nursing coverage in real time; and a trend system configured to allow tracking of progress of an individual patient, and accessible from a remote location.

The system, method, and computer program product can include a plurality of sensors configured for measuring the objective data that integrate with risk level assessments based on the correlated risk values, wherein the pressure ulcer risk level assessments are automatically adjusted with inputted information from the sensors, real-time streaming information from sensors is automatically adjusted for re-position reminders; and an electronic message system configured for sending reminder messages based on the re-position reminders.

The system, method, and computer program product can include a sorting system configured for sorting of patients with similar risk levels; a display unit configured for representing by color indicators similar risk levels; a display screen or printable sheet of at-risk patients to improve nursing workflow; an assessment tool for configured for allowing for re-positioning in real time; a notification device configured for sending re-position reminders for a group of patients; a visual screen configured for displaying at-risk patients simultaneously; and a visual system configured for improving continuity of care during shift changes.

The system, method, and computer program product can include a display device configured for indicating information including patients with a particular medical history, including a symbol which indicates a patient with certain medical history, and a visual display of the information in a nursing workflow.

The system, method, and computer program product can include a device for submitting pressure ulcer prevention measures to nursing outcomes data registries, including a user interface configured to display only when a risk level of a patient is at a predetermined level, an inputted check list from pressure ulcer risk prevention which populates a nursing outcomes data form, an automated documentation tool for nursing staff, which verifies when pressure ulcer prevention tasks are completed, and an automated process between pressure ulcer assessment with data input completion of the nursing outcomes data registries; a device for real-time measurement of nursing outcomes quality indicators, including a quality measurement device configured to bypasses manual entries, and a quality measurement linked to an individual user or an archived period; a device for continuously transmitting pressure ulcer risk assessment and education data remotely via the internet to healthcare providers; and a device for integrating pressure ulcer risk level assessment with robotics technology, including a system configured for instructing a robot when re-positioning is due, the robot configured for assistance with the re-positioning, a documentation system configured for documenting when a patient is re-positioned, and an electronic message system configured to send a message to a user regarding the pressure ulcer risk level assessment and the re-positioning.

From this description, in conjunction with other items, the advantages of the said invention will become clear and apparent more so based upon the hereinafter descriptions and claims, which are supported by drawings with numbers relating to parts, wherein are described in the following sections containing the relating numbers.

BRIEF DESCRIPTION OF THE DRAWINGS

The accompanying drawings, which are incorporated in and constitute a part of the specification, illustrate embodiments of the invention and, together with the description, serve to explain the objects, advantages, and principles of the invention. In the drawings:

FIG. 2 is a GUI illustrating a plurality of patient health factors which are input by a user to identify risk scores for each of the patient health factors, according to one embodiment of the invention;

FIG. 4 is a GUI illustrating patient sorting according to their level of risk of developing a pressure ulcer, according to one embodiment of the invention;

FIG. 5 is a chart illustrating the conversion of inputted data to nursing quality outcomes measurements, according to one embodiment of the invention;

FIG. 6 is a chart illustrating the conversion of inputted data to a trending report of nursing quality measurement and patient safety, according to one embodiment of the invention;

FIG. 7 is a flow chart and a GUI illustrating the export of the inputted information to complete a nursing outcomes database registries form, according to one embodiment of the invention;

DETAILED DESCRIPTION OF PREFERRED EMBODIMENTS

Figure 1:
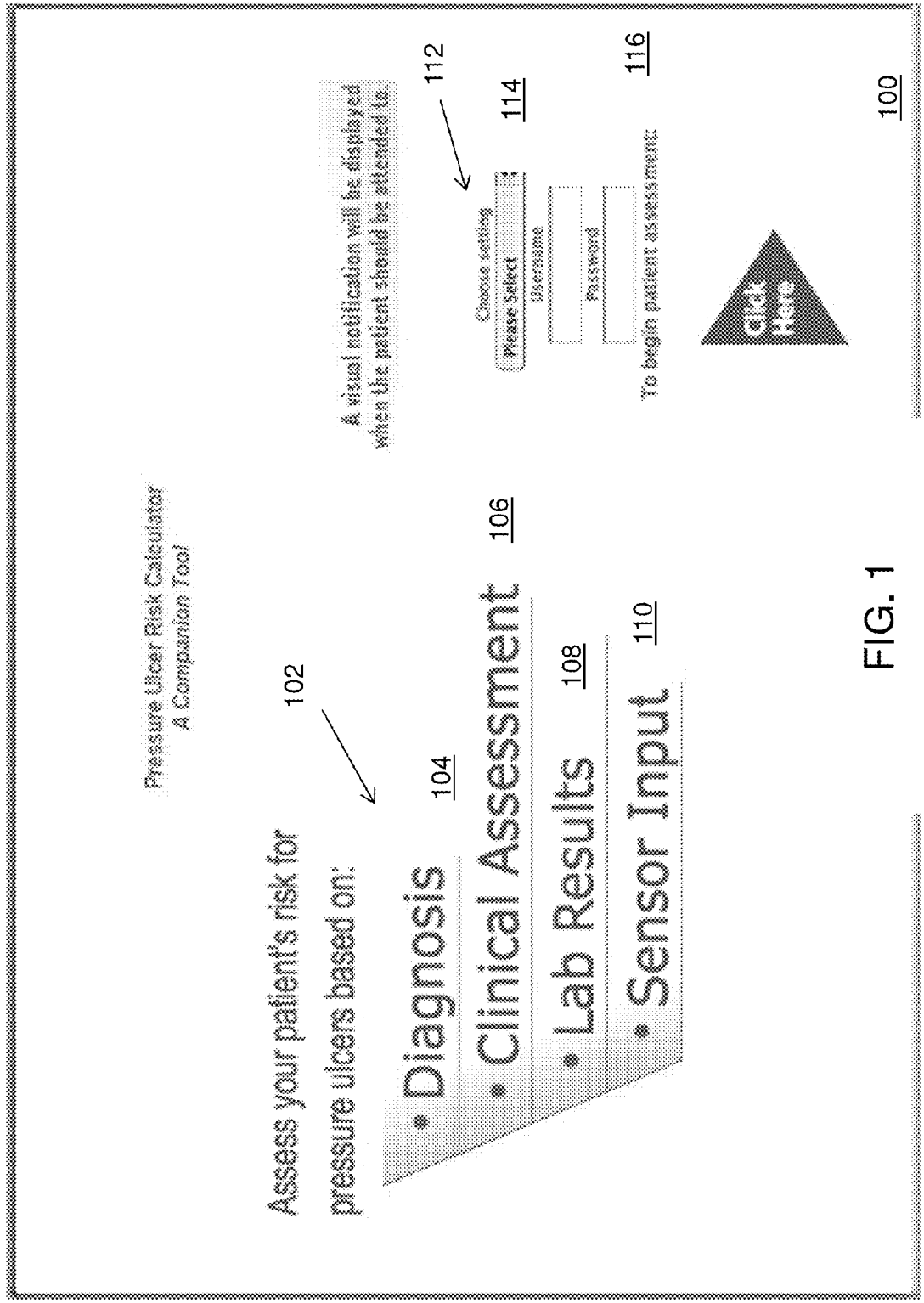
FIG. 1 is a graphical user interface (GUI) for a method of assessing the risk of a patient for developing a pressure ulcer, according to one embodiment of the invention.

After reading this description it will become apparent to one skilled in the art how to implement the invention in various alternative embodiments and alternative applications. However, all the various embodiments of the present invention will not be described herein. It is understood that the embodiments presented here are presented by way of an example only, and not limitation. As such, this detailed description of various alternative embodiments should not be construed to limit the scope or breadth of the present invention as set forth below.

The present invention includes recognition that pressure ulcers can develop in a person who is bedridden, confined to a wheelchair, suffers from particular illness or skin condition, or otherwise subject to extended periods of immobility. An estimated 1.3 to 3 million patients in the United States have pressure ulcers; incidence is highest in older patients, especially when hospitalized or in long-term care facilities. Both intrinsic and extrinsic factors can be involved in the development of such pressure ulcers. Aging increases risk, in part because of reduced subcutaneous fat (e.g., fat layer beneath the skin) and decreased capillary blood flow. Some additional intrinsic factors include impaired mobility, incontinence, skin condition, nutrition, impaired circulation, and altered mental status.

The scope and cost of such pressure ulcers in the United States are significant. Furthermore, no dollar amount can be placed on the cost of human suffering from this debilitating condition.

Implementation of guidelines set forth by the Agency for Health Care Policy and Research (AHCPR) and the 2008 Medicare payment reform have produced improvements in carefully monitored institutions. These studies demonstrated that with diligent nursing care, many pressure ulcers are preventable. However, with staff/patient ratios typically found in many health care facilities, it can be impractical to expect all aspects of the AHCPR guidelines to be followed for all but high-risk patients. The extent of this problem can only be expected to grow as medical advances prolong the life expectancy of seriously ill patients and as the population over the age of 65 expands.

Medical conditions that do not necessarily involve immobility can also increase the risk of the formation of pressure ulcers or similar types of sores. These sores typically occur in the lower extremities, such as neuropathic ulcers that are frequently associated with diabetes, where sores can form as a result of the patient's reduced sensation and/or circulation in their feet, sometimes leading to amputation of the foot or leg, or even death from infection at the site when a sore goes untreated. Venous ulcers (e.g., ulcers due to engorged veins, such as varicose veins) or arterial ulcers can also result from prolonged hydrostatic pressure or ischemia.

Approaches for prevention of pressure sores tend to fall within two broad, but not necessarily mutually exclusive, categories—underpads, pressure redistribution surfaces and electronic sensors and monitoring systems. Among pressure redistribution or support surfaces, proposed solutions include overlays, replacement mattresses, and specialty beds that attempt to reduce the amount of pressure to which tissues are subjected. These approaches tend to vary in effectiveness, practicality of use, economy and maintenance requirements. For example, U.S. Pat. No. 8,011,041 to Hann describes a moisture wicking, breathable pad with electronic pressure sensors. Accordingly, most systems and methods merely address a few of the problems, but none typically consider all of the suitable conditions that can be encountered in patient care, for example, including shear forces, moisture management, bunching (e.g., such as bunch of clothing, bedding), surface texture, breathability, odor control, durability, launderability, and the like. Some systems and methods address pressure ulcer prevention strategies by the use of external devices. However, more needs to be done for accurately assessing the risk levels, an integral step in prevention.

All suitable U.S. acute care hospitals are mandated by the Center for Medicare and Medicaid Services (CMS) to implement pressure ulcer preventive measures and report their outcomes to a National database, such as the National Database for Nursing Quality Indicators (NDNQI). Data collection and reporting to NDNQI are a labor-intensive effort, requiring highly specialized nurses to manually collect data, pore over such data in detail, manually submit the relevant data to an administrator, who then makes the final submission. Furthermore, current clinical algorithms for pressure ulcer risk assessment, such as the Braden Scale, Waterloo Scale or Norton Scale, and the like, have a low predictability of 20~40% due to their subjective bias. The prior systems and methods also lack data analytics for nursing outcomes quality indicator measurements or patient safety measurements, and the like. For example, Table 1 below shows a comparison of pressure ulcer assessment tools.

TABLE 1

Comparison Of Pressure Ulcer Assessment Tools

| | Braden Scale | Norton Scale | Waterloo Scale | Embodiment |
|---|---|---|---|---|
| Criteria | Subjective | Subjective | Subjective | Objective + Subjective |
| Sensor Integration? | No | No | No | Yes |
| Demographic sensitive | No | No | No | Yes |
| Facility sensitive | No | No | No | Yes |
| Visual scale | No | No | No | Yes |
| Nursing Outcomes Data analysis | No | No | No | Yes |
| Patients sorted by risk levels | No | No | No | Yes |
| For multi-users | No | No | No | Yes |
| Enables continuity of care, reduces patient drop | No | No | No | Yes |
| Timer Integration | No | No | No | Yes |
| Useful in surgical patients | No | No | No | Yes |
| Patient/family teaching tool | No | No | No | Yes |
| Nursing teaching tool | No | No | No | Yes |
| Quality improvement tool | No | No | No | Yes |
| Potential for integration with Robotics? | No | No | No | Yes |
| Potential for integration with Genomics | No | No | No | Yes |
| Nursing outcomes documentation tool | No | No | No | Yes |

Overview of Risk Assessment Methodology

Generally, methods and systems described herein allow a user to input patient data and receive an output risk level for that patient which assesses the patient's risk of developing a pressure ulcer. The patient data is a combination of objective and subjective input and allows for inputting information on numerous different categories, or input variables, related to the patient's health. Input variables can include use of a plurality of sensors. Each of the categories includes a risk score for that category, which assesses a risk of the patient developing a pressure ulcer based upon the information input for that particular category. Once the user has input all of the requested patient data, the system evaluates the risk scores for each of the categories of patient data and outputs an overall risk level of the patient's risk of developing a pressure ulcer.

The systems and methods allow a user, such as a nurse, health care professional, caretaker or even the patient to easily enter patient data and automatically receive a risk level indicator. The systems and methods avoid the requirement for manual calculation of risk and provides significant additional patient data categories to increase the accuracy of a risk level assessment. Input values can be uploaded from an existing electronic medical record system. The risk assessment can more accurately predict when patients need more resources or care to prevent the development of pressure ulcers and improve the workflow of the healthcare practitioner with the use of a practical, interactive graphical user interface (GUI) for entering and viewing patient data, risk levels, and the like.

The systems and methods can be implemented as software running on a computer or hosted by a server on a network, so that a plurality of users can access the methodology to continually input new data and provide updated risk level assessments for patients. The user can be presented with one or more graphical user interfaces (GUIs) where they can interact with the system to input data and see a displayed risk level.

In one embodiment, the system stores the overall risk level for each patient over a period of time during several separate risk assessments, such that an overall pattern of risk level can be analyzed to determine if the patient is becoming more or less at risk for developing pressure ulcers. The risk levels can be stored for auditing purposes as well. The system can also store the patient data input by the user for the plurality of patient categories, as this data can be used for future analytic applications and for audit purposes as well. In one embodiment, if a particular category of patient data is not input by the user, the system can trigger an audit alert to determine why the category was not entered or determined.

Selecting Setting

One embodiment of the system and method is illustrated in FIG. 1, which shows a first GUI 100 that can be displayed to a user on a screen, integrates a patient information 102 from objectives 104 and 106, and subjective data 108, and 110. The user can log in at 116 to the system and input patient information to identify the patient for which the risk assessment is being performed. The user at 112 can also be asked to select the type of facility, or setting, that the patient is in, such as a home, hospital, nursing home, home health care facility, hospice, etc. The type of setting 112 can affect the particular risk score that is provided for a particular patient health category. For example, a hospital setting can have increased risk scores for one ore more patient health categories due to the fact that a patient in a hospital setting is generally less healthy and more at risk due to whatever health reason required them to check into the hospital. In contrast, an ambulatory patient receiving care from home can be generally healthy overall and at a lower risk of developing pressure ulcers. The adjustments to the risk scores of the patient data categories can be customized based on known clinical data or based on a continuous assessment of patient data collected by the system for use in better predicting future risk.

Inputting Patient Data

FIG. 2 is an illustration of a GUI screen which provides for inputting patient data into one or more patient data categories. The amount of different patient data categories can vary and be substantial enough to employ multiple patient data input GUI screens. For example, the GUI screen in FIG. 2 shows patient data categories for age/birthday, sex, height, weight, diagnosis, previous ulcers 208, presence of pressure ulcers 210, mobility, fecal incontinence 212, Braden scale and lab values, and the like. However, additional patient data categories that can be useful include recent weight loss 202, recent surgery, functional level, number of hours of sedation, race, skin color matched to a computer screen, such as a mobile phone screen, an electronic tablet, or an iPad, and the like, genomic data, body mass index (BMI), pre-operative or peri-operative time frames, pain level, number of devices attached to the patient, medications or other treatments, blood pressure, type of bed and mattress, alternative or complementary therapies, sacral nerve implantation/stimulation, sensors that capture movement, moisture, temperature, or level of proteins leaked from distressed skin, and the like, mattress pressure mapping, and the like. These categories can affect the risk of a patient developing a pressure ulcer, and so a risk score can be determined for any and all of these categories if they are entered by the user for a particular patient.

Patient Data Category Risk Values

The type of data entered for each patient data category is then correlated with a stored risk score based on the type of input received. The risk scores for each of the patient data categories can be classified, in one embodiment, as low, intermediate and high, with corresponding numerical scores of 1-4, 5-7 and 8-10 being provided to more accurately classify the risk. For example, if the patient is moderately overweight (e.g., based on the combination of their height and weight), an intermediate risk score of between 5 and 7 can be assessed. However, if the patient is morbidly obese, the risk score can be elevated to an 8 or higher (e.g., the high risk category), as the patient is probably unlikely to want to move around.

Each patient data category has a corresponding stored risk value associated with each possible data entry in each patient data category. The risk values can be determined based on any suitable methodology which evaluates the pressure ulcer risks for each possible data entry in each patient data category. The risk values can be determined from clinical data, generally accepted medical literature and research, data from the system itself as to whether the risk values predicted in the past correlate with actual observations of the patient, and other medical knowledge from literature or a user, and the like. The user can be able to customize the risk values based on their own unique setting or patient base. Additionally, the risk values can be updated regularly to reflect changes in medical knowledge or analysis of past data.

In one embodiment, the Diagnosis category 204 shown in FIG. 2 provides a lengthy drop-down menu of possible conditions which the patient can be diagnosed with. Different list of diagnoses 206 are presented for different facility setting. The user can select one or more conditions on the list, which can be a comprehensive list of clinical or medically known conditions, and the like, known to be pertinent to pressure ulcer risks.

By including numerous patient data categories, the accuracy of a resulting risk assessment can be improved, as these additional patient data categories are relevant in determining the risk of pressure ulcers to a patient. The GUI can also generate a trending report 214.

Determining the Risk Level

Once the patient data has been entered, the system and method calculate a risk level for the patient based on the risk values corresponding to each of the patient data categories. In one embodiment, the determination of the risk level can be made by looking for the highest risk score associated with the input data of the patient data categories. For example, if a diagnosis of "Diabetes" is entered in the diagnosis field on FIG. 2, where diabetes 206 has a corresponding risk value of 5, an overall risk level of "5" can be output to the user, if no other patient data category has a higher risk value. However, if patient data entered into the "Mobility" category indicates that the patient is immobile or confined to a bed, such that the corresponding risk value is a "10," the overall risk level displayed to the user can be a "10," since this is higher than the "7" produced by the Diabetes diagnosis. The actual risk values provided here are exemplary and can vary. Therefore, one embodiment of the system and method determine an overall risk level by looking for the highest risk score that occurs based on the patient data inputted into the system.

In another embodiment, the risk level can be determined by evaluating more than one risk value to provide some type of weight or other valuation factor to one risk score depending upon its significance (or e.g., insignificance). The risk scores can be averaged or have a median risk score determined to reflect an overall generalization of the risk level.

Displaying Risk Levels

Figure 3:
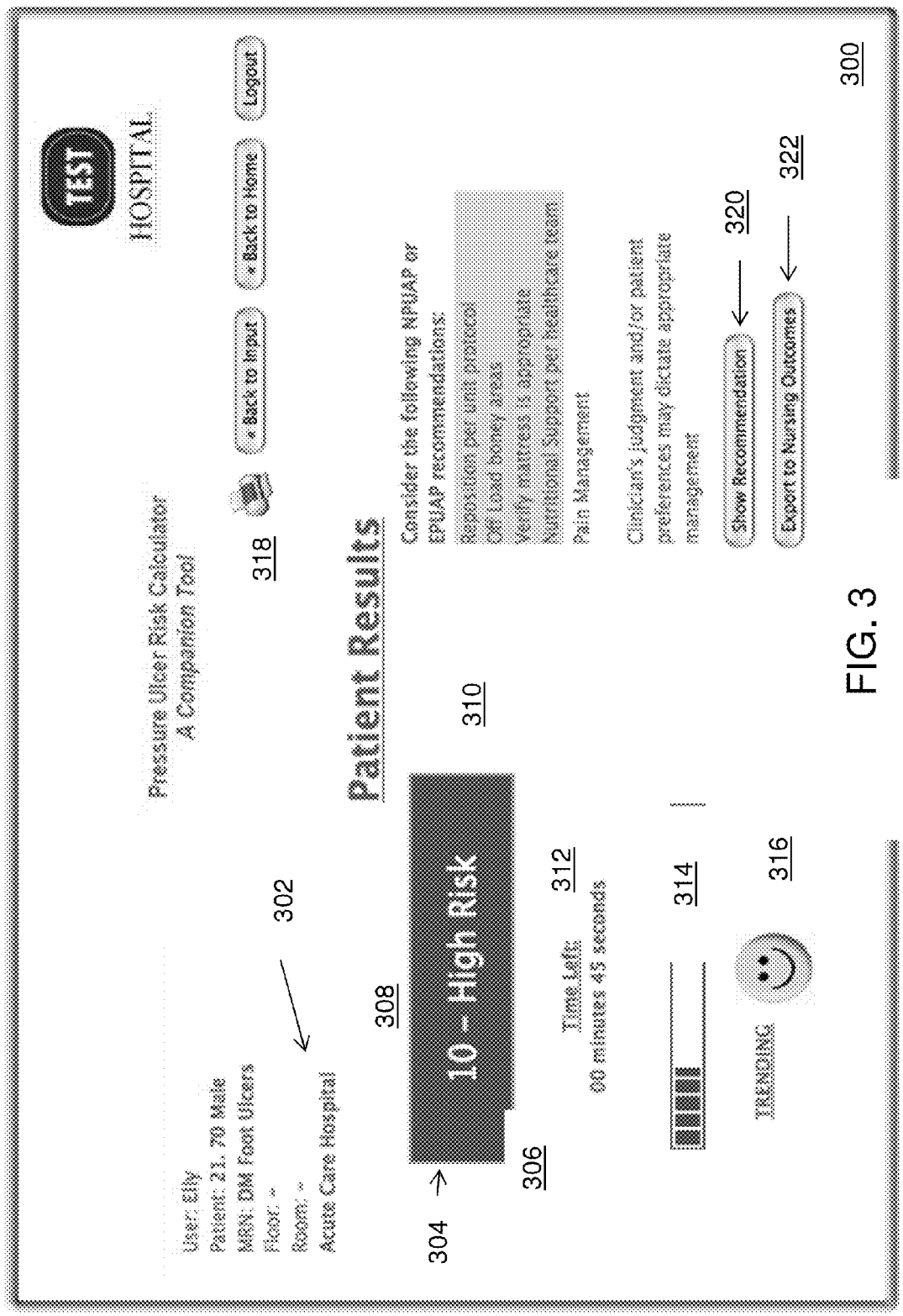
FIG. 3 is a GUI illustrating a resulting risk assessment level of risk of the patient developing a pressure ulcer based on the inputted patient health factors, according to one embodiment of the invention.

For a given care facility setting 302, the risk level can be displayed to the user with a numerical, symbolic or color-coded GUI 300, as illustrated in FIG. 3. In this embodiment, the risk level is provided as a color-coded bar 304 to provide a simple visual cue to the user to indicate the level 308 and severity of the risk 310. For example, the bar in FIG. 3 which displays "10" can be red in color at 306 to indicate a high risk, while a risk level of 5-7 can be an intermediate risk level illustrated by a yellow color, and a risk level of 1-4 can be a low risk level represented by a green color, and the like. The colors and the ranges of numerical risk levels which fall within these colors can be varied, as needed.

The GUI illustrated in FIG. 3 can also provide recommendations to the user based upon the determined risk level of the patient. A printable copy via 318 of the GUI can be used for patient education. In one embodiment, the user can be provided with several prevention recommendations 320 to reduce the risk or avoid developing pressure ulcers in a high risk patient. The system and method can also indicate how and when the patient should be turned via indicator 312. To encourage the use of a timer 314, Start Time button (not shown) turns into a smiling face 316. The system and method can propose therapeutic options based on multiple sensor 1216 inputs of FIG. 12 or communications with robotic technology for re-positioning or injury prevention analysis. The GUI can include data export capability to the nursing outcomes data registries form via 322.

Patient Sorting by Risk Levels

Figure 4:
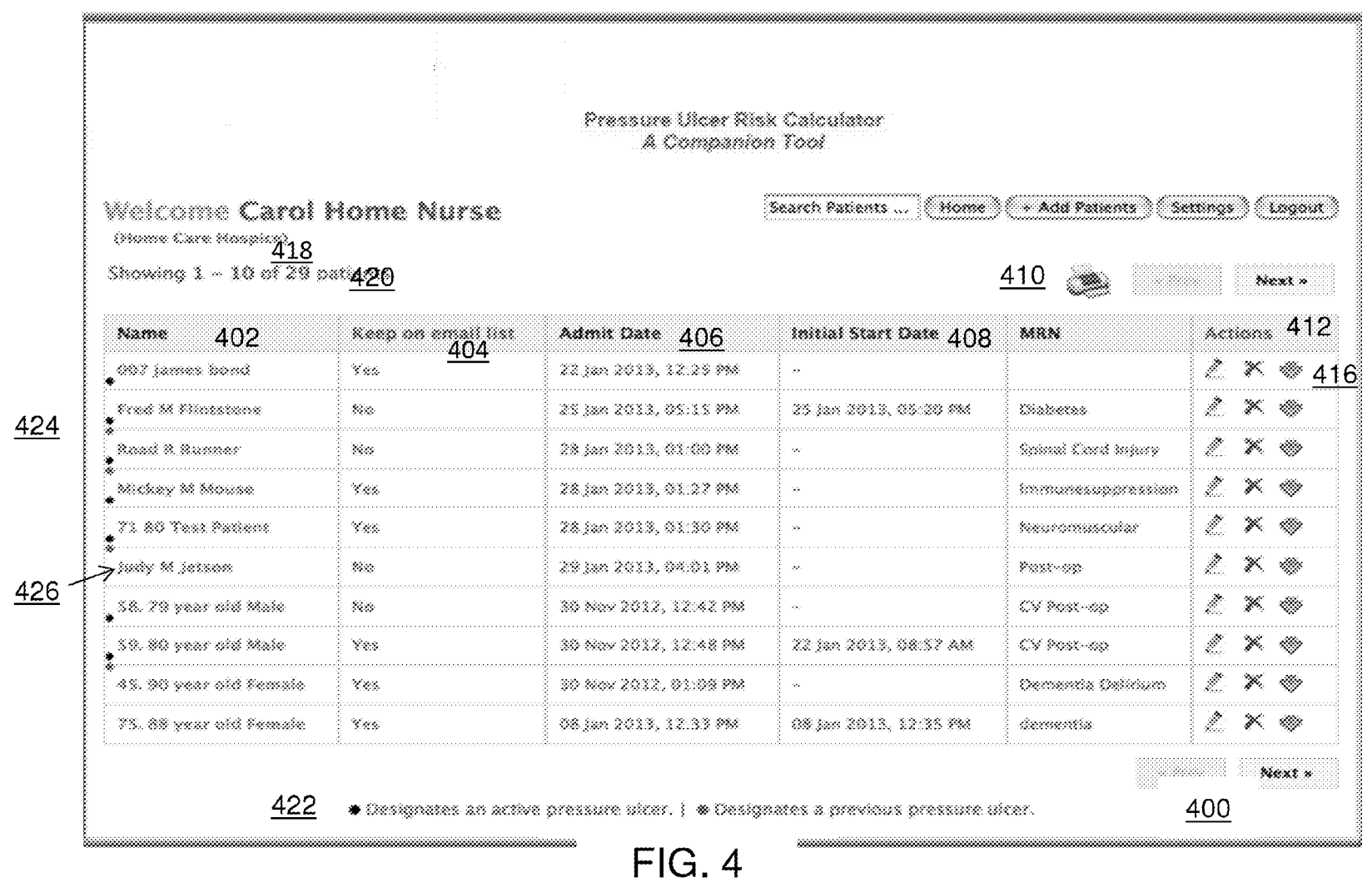

Once the patient data has been entered, the system and method calculate risk levels for the patients and sorts them in a color-coded list 400 of FIG. 4. In one embodiment, as illustrated by a GUI in FIG. 4, facility selection 418 identifies the type of patients presented on the screen. Area 420 shows number of patients within the group. Column 402 depicts a list of patients visible to the user or multiple users, as they are sorted with highest risk level on top at 424. For example, a red color can be used for high risk group, yellow for intermediate risk group, green for low risk group, and blue for patients whose input data are incomplete at 426.

As illustrated in FIG. 4, a user can choose to be notified by any suitable device, including various ring tones or telephone, for an individual or a group of patients at 404. Columns 406 and 408 assess time elapsed between admission and documentation of pressure ulcer prevention, which tracks nursing quality and documents for the nurse outcomes data registries form 700 of FIG. 7. Column 412 illustrates possible actions by the user. Inputted patient data can transfer pertinent data 416 to nursing outcomes quality measurement sheet 500 of FIG. 5 and patient outcomes indicator 514 of FIG. 5. Improved continuity of care and prevention of patient drop are ensured by designating patients with active pressure ulcers and past history of a pressure ulcer with a suitable indicator 422. Multiple users also can print via button 410 a patient sorted list to improve continuity of care and minimize patient drop.

Nursing Quality Measurement Reports

A table in FIG. 5 illustrates one embodiment of an easy-to-follow nursing outcomes quality report 500, which provides connectivity between Risk Assessment Input GUI 200 and Risk Level Results GUI 300. Accordingly, manual and laborious calculation need not be necessary to generate such a report. When patient data are entered, the system and method calculate nursing quality measurement 518 and 520, as well as patient safety measurement 514. Similarly, other nursing quality parameters 504, 506, 508, 510, 516, 518, and 520 can be displayed in such a report.

A table in FIG. 6 illustrates one embodiment of easy-to-read, visual trending report focused on nursing outcomes quality measurement. When the total number of patients 604 is submitted manually or automatically from an electronic medical record database, a relevant patient subset 606, patients admitted with pressure ulcers 608, stage of pressure ulcer 610, and their trend 603 and 611 are displayed so as to become more intuitive for the user. Similarly, nursing quality measurement, for example, agency-acquired pressure ulcer cases 612 and 616, as well as prevalence 614 can be presented and displayed in sequence. Information presented and displayed in such a manner provides various advantages, for example, including incidence of agency-caused pressure ulcers 612, which can show a reduction, reflecting good nursing care, and the like.

A GUI in FIG. 7 illustrates the connectivity between information from the Risk Assessment Input GUI 200 with the nursing outcomes data collection form 702. Exporting data directly at step 701 to the data collection form improves the accuracy and time saved in collecting, verifying, and submitting data through various personnel. For example, submitted answers 706, 707, 708, 710, 712, 714, and 716 for a patient 704 can be exported from the GUI 200. Export Data button 702 exports relevant nursing quality information to table 502 of FIG. 5.

Figure 8:
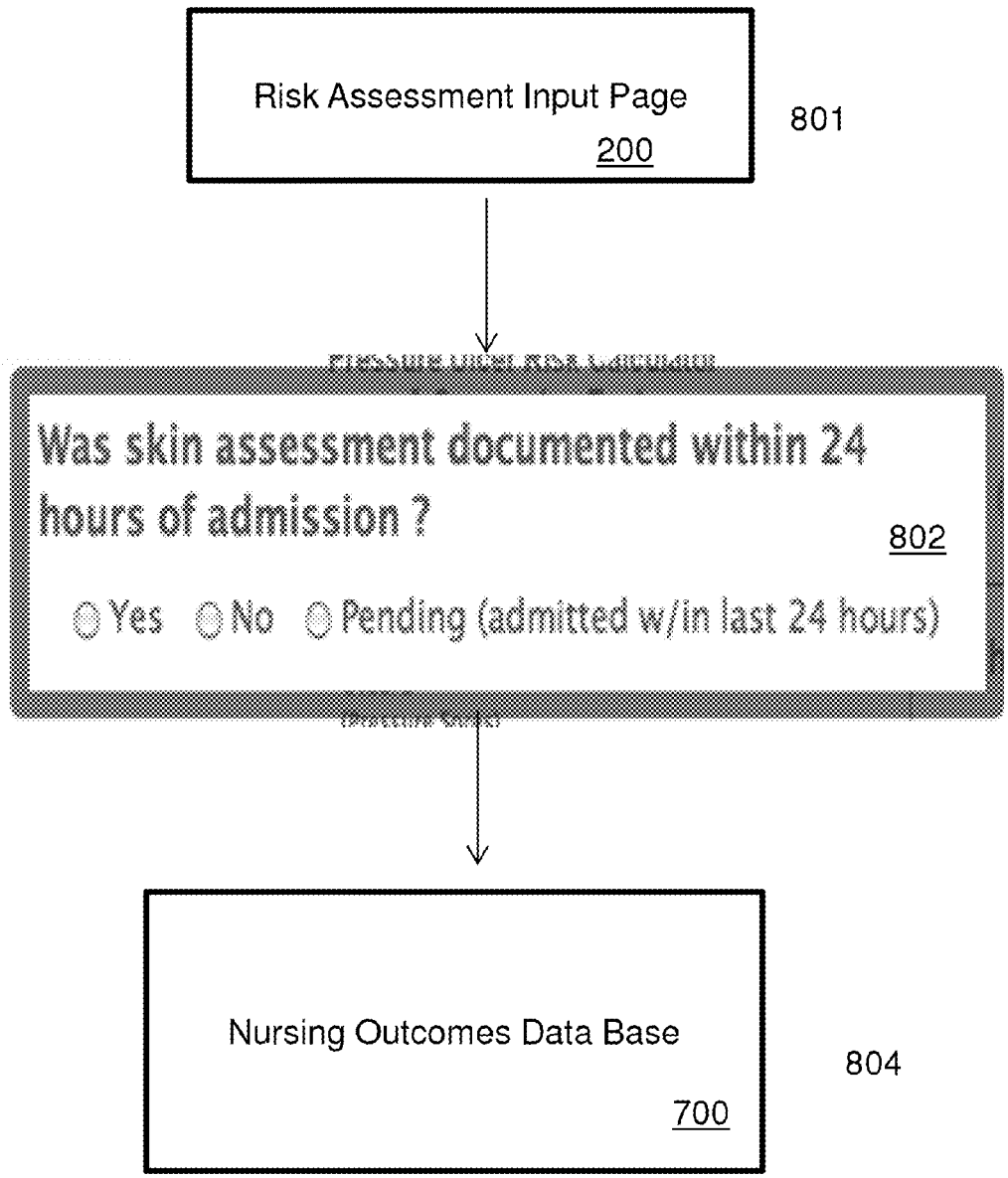
FIG. 8 is a flow chart and a GUI illustrating the export of the risk level assessment input sheet to the nursing outcomes database registries form, according to one embodiment of the invention.

A GUI in FIG. 8 illustrates a further export connectivity step 802 between the Risk Assessment Input GUI 200 with the Nursing Outcomes Data Collection form 700 at step 804. For example, response to a timely skin assessment 802 is exported to the database form 700 of FIG. 7, while documentable step 504 of FIG. 5 and trackable step 706 of FIG. 7 are automatically populated.

Figure 9:
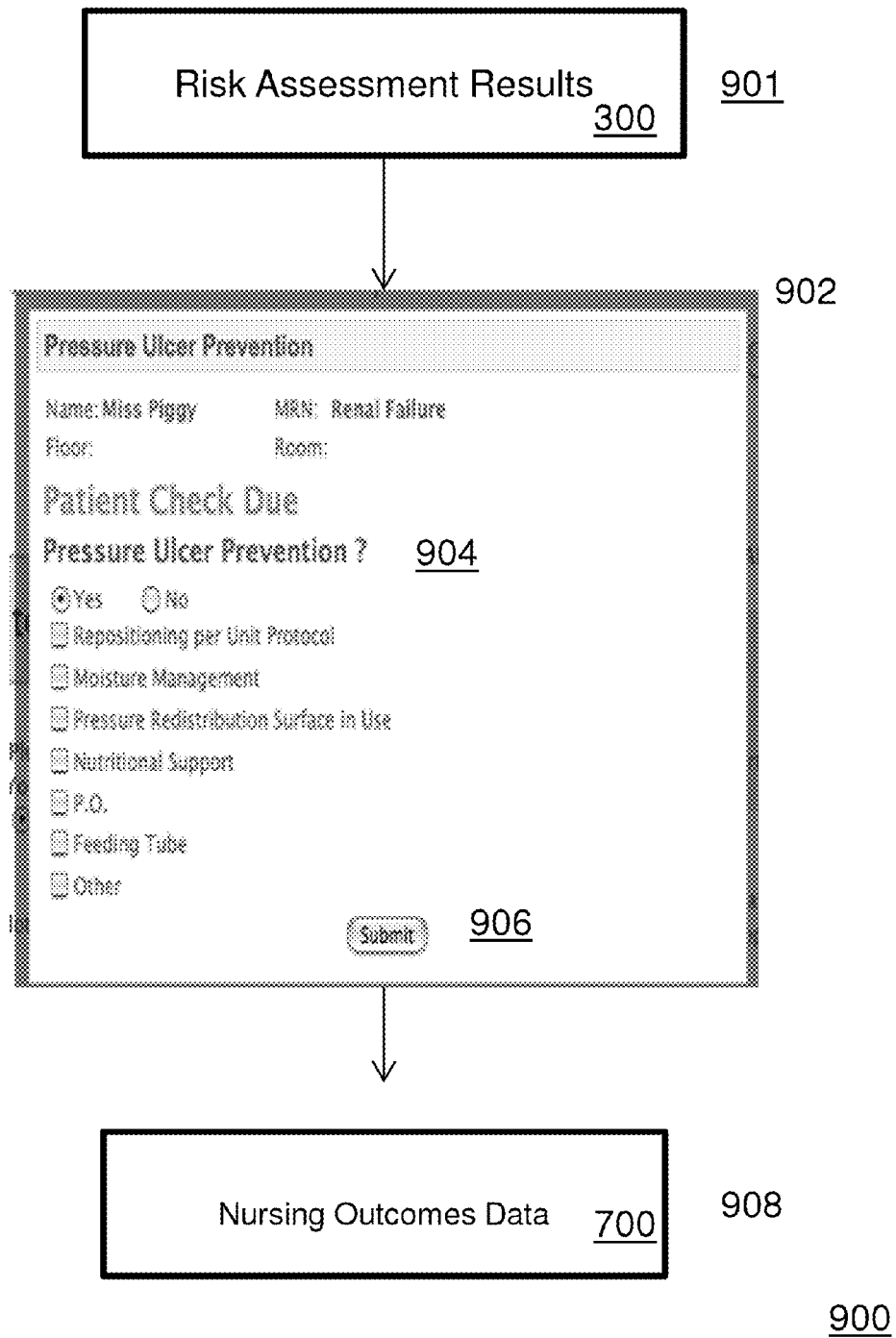
FIG. 9 is a flow chart and a GUI illustrating the export of the risk level assessment results sheet to the nursing outcomes database registries form, according to one embodiment of the invention.

A GUI in FIG. 9 illustrates the export connectivity step 901 between Risk Assessment Results GUI 300 with the nursing outcomes data collection form 700 at step 908. For example, for an at-risk patient, the user indicates appropriate pressure ulcer prevention check-off steps 904, which are documented at step 908 in the form 700 when submitted at via a submit button step 906.

Figure 10:
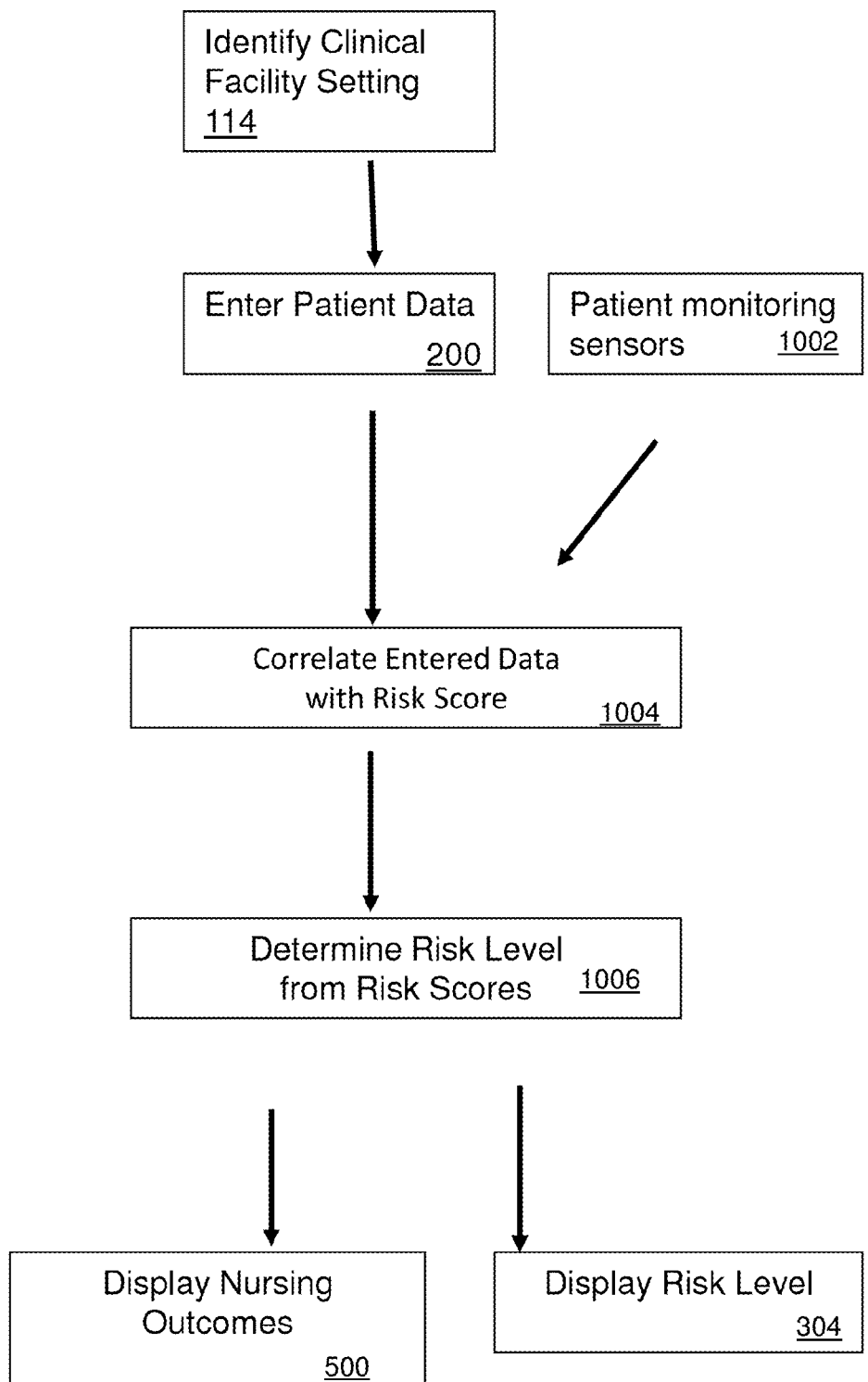
FIG. 10 is a flow chart illustrating the pressure ulcer risk level display to the nursing quality outcomes measurements, according to one embodiment of the invention.

FIG. 10 illustrates a flowchart 1000 describing a relationship between the pressure ulcer risk assessment GUI 100 with the nursing outcomes quality measurement GUI 500 and patient safety step 514 of form 500. The clinical facility setting step 114 is identified to adjust the corresponding risk scores of the patient data categories. The patient data is then entered into the system in the appropriate categories on the GUI 200. The entered patient data is correlated with stored risk values for each category and each type of data entered for each category in the GUI 200. The risk levels are then determined based on the risk scores of each of the patient data categories. Sensor data from various patient monitoring sensors at step 1002 are correlated with the determined risk score at step 1004. Data from the risk level GUI 300 at step 1006 can be exported to the nursing outcomes quality measurement form 500. Risk level can displayed as a colored bar 304 of FIG. 3, as a numerical score, based on voice, electronic mail, predetermined vibration signal, and the like.

Figure 11:
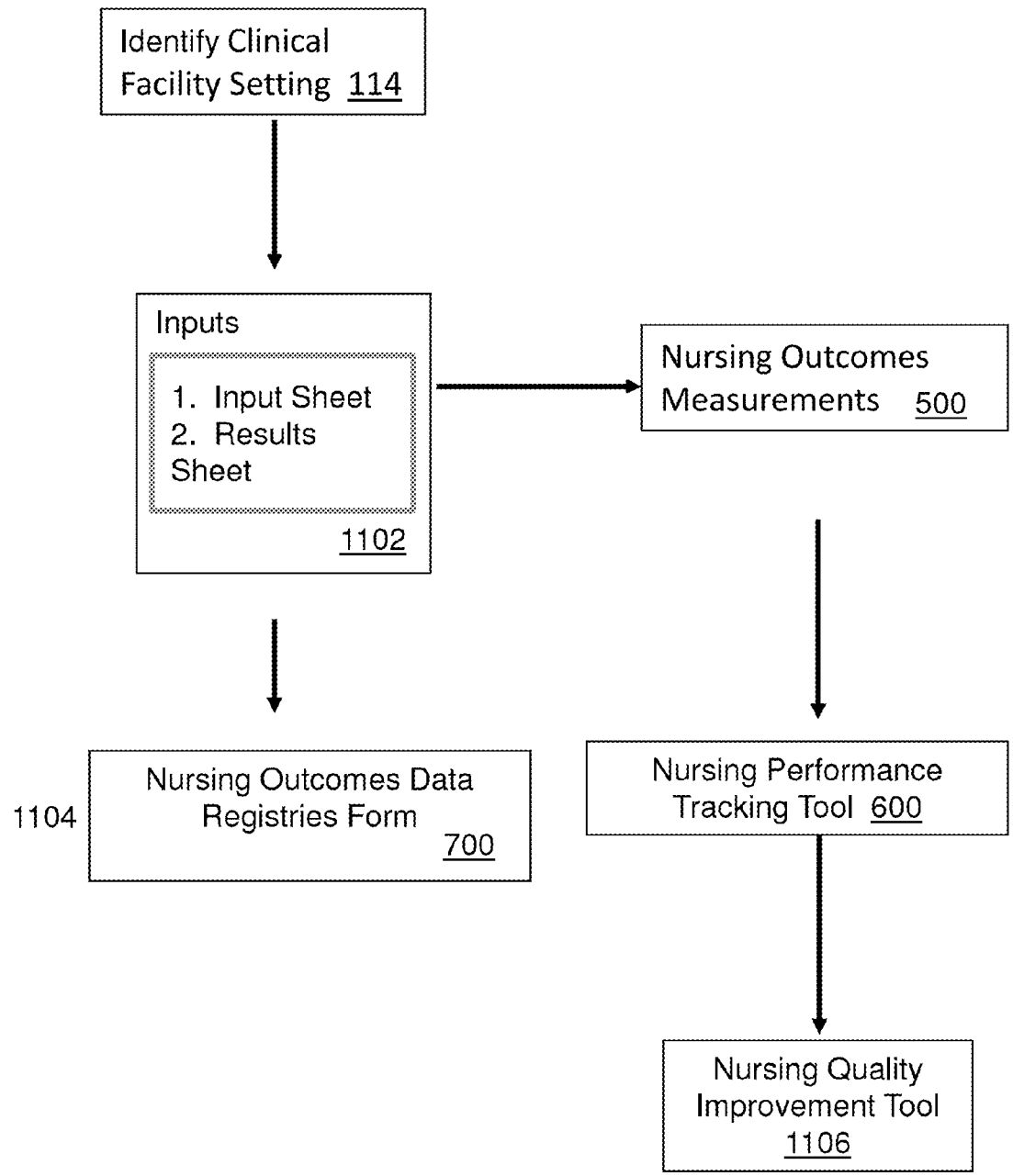
FIG. 11 is a flow chart illustrating the use of pressure ulcer risk assessment as a nursing performance and improvement tool, according to one embodiment of the invention.

FIG. 11 illustrates a flowchart 1100 describing a relationship between the pressure ulcer risk assessment GUI 100 with the nursing outcomes data collection form 700 and a nursing quality improvement tool at step 1106. The user selects a clinical facility setting at step 114, and the system and method generate input and output pages at step 1102. Data are exported to nursing outcomes data form 700 at step 1104 or nursing outcomes quality measurements table 500. The user can use this report for further trending 600 and to improve nursing quality at step 1106.

Computer-Implemented Embodiment

Figure 12:
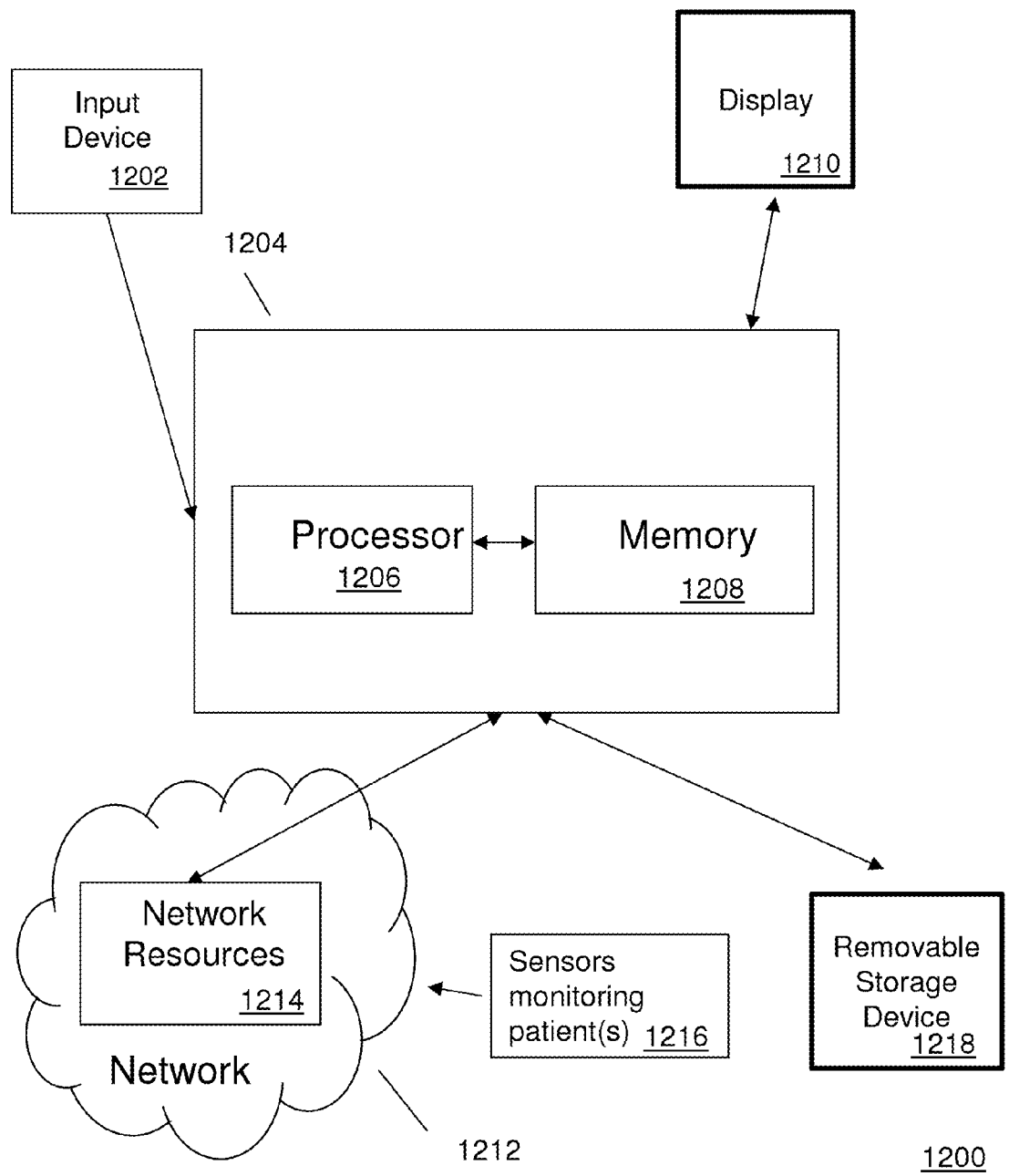
FIG. 12 is a block diagram that illustrates an embodiment of a computer/server system upon which an embodiment of the inventive methodology can be implemented.

FIG. 12 is a block diagram that illustrates an embodiment of a computer/server system 1200 upon which an embodiment of the inventive methodology can be implemented. The system 1200 includes a computer/server platform 1204 including a processor 1206 and memory 1208, which operate to execute instructions and maintain a database. The term "computer-readable storage medium," as used herein can refer to any tangible medium, such as a disk or semiconductor memory, that participates in providing instructions to processor 1206 for execution. Additionally, the computer platform 1204 receives input from a plurality of input devices 1202, such as a keyboard, mouse, touch device or verbal command. The computer platform 1204 can additionally be connected to a removable storage device 1218, such as a portable hard drive, optical media (e.g., CD or DVD), disk media or any other tangible medium from which a computer can read executable code. The computer platform can further be connected to network resources 1214, which connect to the Internet or Intranet other components of a local public or private network. The network resources 1214 and sensors capable of monitoring patient(s) 1216 can provide instructions and data to the computer platform from a remote location on a network 1212. The connections to the network resources 1214 can be via wireless protocols, such as the 802.11 standards, Bluetooth® or cellular protocols, or via physical transmission media, such as cables or fiber optics. The network resources can include storage devices for storing data and executable instructions at a location separate from the computer platform 1218. The computer interacts with any suitable type of display 1210 to output data and other information to a user, as well as to request additional instructions and input from the user. The display 1210 can therefore further act as an input device 1202 for interacting with a user.

The computer/server system 1200 can be implemented, for example, for an anonymous patient user, and include a standalone executable program. Any suitable user, such as a patient or a caregiver, can access such program via the internet or any available mobile technology, or have another user input data remotely via telephone. The result can be displayed or verbally presented or printed for view.

Accordingly, the above-described devices and subsystems of the illustrative embodiments can include, for example, any suitable servers, workstations, PCs, laptop computers, PDAs, Internet appliances, handheld devices, cellular telephones, wireless devices, other devices, and the like, capable of performing the processes of the illustrative embodiments. The devices and subsystems of the illustrative embodiments can communicate with each other using any suitable protocol and can be implemented using one or more programmed computer systems or devices.

One or more interface mechanisms can be used with the illustrative embodiments, including, for example, Internet access, telecommunications in any suitable form (e.g., voice, modem, and the like), wireless communications media, and the like. For example, employed communications networks or links can include one or more wireless communications networks, cellular communications networks, G3 communications networks, Public Switched Telephone Network (PSTNs), Packet Data Networks (PDNs), the Internet, intranets, cloud computing networks, a combination thereof, and the like.

It is to be understood that the described devices and subsystems are for illustrative purposes, as many variations of the specific hardware used to implement the illustrative embodiments are possible, as will be appreciated by those skilled in the relevant art(s). For example, the functionality of one or more of the devices and subsystems of the illustrative embodiments can be implemented via one or more programmed computer systems or devices.

To implement such variations as well as other variations, a single computer system can be programmed to perform the special purpose functions of one or more of the devices and subsystems of the illustrative embodiments. On the other hand, two or more programmed computer systems or devices can be substituted for any one of the devices and subsystems of the illustrative embodiments. Accordingly, principles and advantages of distributed processing, such as redundancy, replication, and the like, also can be implemented, as desired, to increase the robustness and performance of the devices and subsystems of the illustrative embodiments.

The devices and subsystems of the illustrative embodiments can store information relating to various processes described herein. This information can be stored in one or more memories, such as a hard disk, optical disk, magneto-optical disk, RAM, and the like, of the devices and subsystems of the illustrative embodiments. One or more databases of the devices and subsystems of the illustrative embodiments can store the information used to implement the illustrative embodiments of the present inventions. The databases can be organized using data structures (e.g., records, tables, arrays, fields, graphs, pigeons, trees, lists, and the like) included in one or more memories or storage devices listed herein. The processes described with respect to the illustrative embodiments can include appropriate data structures for storing data collected and/or generated by the processes of the devices and subsystems of the illustrative embodiments in one or more databases thereof.

All or a portion of the devices and subsystems of the illustrative embodiments can be conveniently implemented using one or more general purpose computer systems, microprocessors, digital signal processors, micro-controllers, and the like, programmed according to the teachings of the illustrative embodiments of the present inventions, as will be appreciated by those skilled in the computer and software arts. Appropriate software can be readily prepared by programmers of ordinary skill based on the teachings of the illustrative embodiments, as will be appreciated by those skilled in the software art. Further, the devices and subsystems of the illustrative embodiments can be implemented on the World Wide Web. In addition, the devices and subsystems of the illustrative embodiments can be implemented by the preparation of application-specific integrated circuits or by interconnecting an appropriate network of conventional component circuits, as will be appreciated by those skilled in the electrical art(s). Thus, the illustrative embodiments are not limited to any specific combination of hardware circuitry and/or software.

Stored on any one or on a combination of computer readable media, the illustrative embodiments of the present inventions can include software for controlling the devices and subsystems of the illustrative embodiments, for driving the devices and subsystems of the illustrative embodiments, for enabling the devices and subsystems of the illustrative embodiments to interact with a human user, and the like. Such software can include, but is not limited to, device drivers, firmware, operating systems, development tools, applications software, and the like. Such computer readable media further can include the computer program product of an embodiment of the present inventions for performing all or a portion (if processing is distributed) of the processing performed in implementing the inventions. Computer code devices of the illustrative embodiments of the present inventions can include any suitable interpretable or executable code mechanism, including but not limited to scripts, interpretable programs, dynamic link libraries (DLLs), Java classes and applets, complete executable programs, Common Object Request Broker Architecture (CORBA) objects, and the like. Moreover, parts of the processing of the illustrative embodiments of the present inventions can be distributed for better performance, reliability, cost, and the like.

As stated above, the devices and subsystems of the illustrative embodiments can include computer readable medium or memories for holding instructions programmed according to the teachings of the present inventions and for holding data structures, tables, records, and/or other data described herein. Computer readable medium can include any suitable medium that participates in providing instructions to a processor for execution. Such a medium can take many forms, including but not limited to, non-volatile media, volatile media, transmission media, and the like. Non-volatile media can include, for example, optical or magnetic disks, magneto-optical disks, and the like. Volatile media can include dynamic memories, and the like. Transmission media can include coaxial cables, copper wire, fiber optics, and the like. Transmission media also can take the form of acoustic, optical, electromagnetic waves, and the like, such as those generated during radio frequency (RF) communications, infrared (IR) data communications, and the like. Common forms of computer-readable media can include, for example, a floppy disk, a flexible disk, hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read.

Although the present invention is described in terms of detecting, preventing, and the like, pressure ulcers, the present invention can provide for peroperative related choices, and the like, based on the teachings of the present invention, for example, via a drop down box of the GUI 100 of FIG. 1, as will be appreciated by those skilled in the relevant art(s).

Although the present invention is described in terms of detecting, preventing, and the like, pressure ulcers, the present invention can be applied to pediatric patients, applications, and the like, based on the teachings of the present invention, as will be appreciated by those skilled in the relevant art(s).

The above description of disclosed embodiments is provided to enable any person skilled in the art to make or use the invention. Various modifications to the embodiments will be readily apparent to those skilled in the art, the generic principals defined herein can be applied to other embodiments without departing from spirit or scope of the invention. Thus, the invention is not intended to be limited to the embodiments shown herein but is to be accorded the widest scope consistent with the principals and novel features disclosed herein.

What is claimed is:

1. A computer implemented system for assessing a risk of developing pressure ulcers, the system comprising:
   a user input unit configured to receive a plurality of patient data, the plurality of patient data for each patient data comprising facility setting information indicative of a location of a patient receiving care and objective and subjective information of said patient for a plurality of categories of said patient data, wherein the facility setting information includes a home facility setting, a hospital facility setting, a nursing home facility setting, a home health care facility setting, and a hospice facility setting,
   a national database is populated based on the plurality of patient data, including National Database for Nursing Quality Indicators, and a nursing outcomes data registry;
   a correlation unit configured to determine a corresponding risk value of developing a pressure ulcer for each category of the patient data for each patient, based on the patient data received in each category, adjust the corresponding risk value for each category of the patient data for each patient based on the facility setting information, and correlate the corresponding risk value for each category of the patient data for each patient based on the patient data and the facility setting information;
   a risk determination unit configured to determine a level of risk of each patient developing a pressure ulcer based on the correlated risk values of the plurality of categories of the patient data for each patient; the level of risk including a high risk level, a medium risk level, and a low risk level; and
   a plurality of sensors, configured to measure the objective data of a respective patient, that integrate with the risk determination unit to automatically adjust the level of risk of said respective patient based on the correlated risk values of the plurality of categories of the patient data of the respective patient and inputted information from the plurality of sensors;

wherein
   the risk determination unit is configured to default the level of risk based on the highest correlated risk value of the plurality of categories of the patient data,
   the risk determination unit is configured to display, via a display unit, based on the plurality of patient data, patient information with color coded indicators corresponding to patients with an active pressure ulcer, and patients with a previous pressure ulcer, and
   the risk determination unit is configured to, based on the plurality of patient data and the inputted information from the plurality of sensors of the respective patient, determine and display a patient safety measurement, and nursing quality information, including a nursing quality measurement, and a nursing performance measurement;
wherein real-time streaming information from the plurality of sensors is automatically adjusted for re-position reminders for the plurality of patients;
an electronic message system configured for sending reminder messages based on the re-position reminders for the plurality of patients; and
wherein the user input unit configured for submitting pressure ulcer risk prevention measures to the nursing outcomes data registry, including
   a user interface configured to display only when a risk level of a patient is at a predetermined level,
   an inputted check list from pressure ulcer risk prevention which populates a nursing outcomes data form,
   an automated documentation tool for nursing staff, which verifies when pressure ulcer prevention tasks are completed, and
   an automated process between pressure ulcer assessment with data input completion of the nursing outcomes data registries;
a device for real-time measurement of nursing outcomes quality indicators, including a quality measurement device configured to bypasses manual entries, and a quality measurement linked to an individual user or an archived period;
a device for continuously transmitting pressure ulcer risk assessment and education data remotely via the internet to healthcare providers; and
a device for integrating pressure ulcer risk level assessment with robotics technology, including
   a system configured for instructing a robot when re-positioning is due, the robot configured for assistance with the re-positioning,
   a documentation system configured for documenting when a patient is re-positioned, and
   an electronic message system configured to send a message to a user regarding the pressure ulcer risk level assessment and the re-positioning.

2. The system of claim 1, further comprising:
a color-coded visual display configured to display risk levels corresponding to the correlated risk values, and including a numerical and word display;
a multi-user platform configured to allow viewing of the risk levels for allocation of nursing coverage in real time; and
a trend system configured to allow tracking of progress of an individual patient, and accessible from a remote location.

3. The system of claim 1, further comprising:
a sorting system configured to sort of the plurality of patients with similar risk levels;
the display unit configured for representing by color indicators similar risk levels;

a display screen or printable sheet of at-risk patients to improve nursing workflow;
an assessment tool configured to allow for re-positioning in real time;
a notification device configured for sending re-position reminders for a group of patients;
a visual screen configured for displaying at-risk patients simultaneously; and
a visual system configured for improving continuity of care during shift changes.

4. The system of claim 1, further comprising: the display unit configured to indicate information including patients with a particular medical history, including a symbol which indicates a patient with certain medical history, and a visual display of the information in a nursing workflow.

5. A computer implemented method for assessing a risk of developing pressure ulcers, the method comprising:
receiving a plurality of patient data with a user input unit, the plurality of patient data for each patient data comprising facility setting information indicative of a location of a patient receiving care and objective and subjective information of said patient for a plurality of categories of said patient data, wherein the facility setting information includes a home facility setting, a hospital facility setting, a nursing home facility setting, a home health care facility setting, and a hospice facility setting,
a national database is populated based on the plurality of patient data, including National Database for Nursing Quality Indicators, and a nursing outcomes data registry;
determining with a correlation unit a corresponding risk value of developing a pressure ulcer for each category of the patient data for each patient, based on the patient data received in each category;
adjusting with the correlation unit the corresponding risk value for each category of the patient data for each patient based on the facility setting information, and
correlating with the correlation unit the corresponding risk value for each category of the patient data for each patient based on the patient data and facility setting information;
determining with a risk determination unit a level of risk for each patient developing a pressure ulcer based on the correlated risk values of the plurality of categories of the patient data for each patient, the level of risk including a high risk level, a medium risk level, and a low risk level;
measuring with a plurality of sensors, the objective data of a respective patient, that integrate with the risk determination unit to automatically adjust the level of risk of said respective patient based on the correlated risk values of the plurality of categories of the patient data of the respective patient and inputted information from the plurality of sensors;
defaulting with the risk determination unit the level of risk based on the highest correlated risk value of the plurality of categories of the patient data,
displaying with a display unit connected to the risk determination unit, based on the plurality of patient data, patient information with color coded indicators corresponding to patients with an active pressure ulcer, and patients with a previous pressure ulcer; and
determining and displaying with the risk determination unit, based on the plurality of patient data and the inputted information from the plurality of sensors of the respective patient, a patient safety measurement, and nursing quality information, including a nursing quality measurement, and a nursing performance measurement;
wherein real-time streaming information from sensors is automatically adjusted for re-position reminders for the plurality of patients;
an electronic message system configured for sending reminder messages based on the re-position reminders for the plurality of patients; and
wherein the user input unit configured for submitting pressure ulcer risk prevention measures to the nursing outcomes data registry, including
a user interface configured to display only when a risk level of a patient is at a predetermined level,
an inputted check list from pressure ulcer risk prevention which populates a nursing outcomes data form,
an automated documentation tool for nursing staff, which verifies when pressure ulcer prevention tasks are completed, and
an automated process between pressure ulcer assessment with data input completion of the nursing outcomes data registries;
a device for real-time measurement of nursing outcomes quality indicators, including a quality measurement device configured to bypasses manual entries, and a quality measurement linked to an individual user or an archived period;
a device for continuously transmitting pressure ulcer risk assessment and education data remotely via the internet to healthcare providers; and
a device for integrating pressure ulcer risk level assessment with robotics technology, including
a system configured for instructing a robot when re-positioning is due, the robot configured for assistance with the re-positioning,
a documentation system configured for documenting when a patient is re-positioned, and
an electronic message system configured to send a message to a user regarding the pressure ulcer risk level assessment and the re-positioning.

6. The method of claim 5, further comprising:
displaying with a color-coded visual display risk levels corresponding to the correlated risk values, and including a numerical and word display;
viewing with a multi-user platform the risk levels for allocation of nursing coverage in real time; and
tracking with a trend system progress of an individual patient, and accessible from a remote location.

7. The method of claim 5, further comprising:
sorting of the plurality of patients with similar risk levels with a sorting system;
representing by color indicators similar risk levels with the display unit;
providing a display screen or printable sheet of at-risk patients to improve nursing workflow;
allowing for re-positioning in real time with an assessment tool;
sending re-position reminders for a group of patients with a notification device;
displaying at-risk patients simultaneously with a visual screen; and improving continuity of care during shift changes with a visual system.

8. The method of claim 5, further comprising: indicating information with the display unit and including patients with a particular medical history, including a symbol which indicates a patient with certain medical history, and a visual display of the information in a nursing workflow.

9. A computer program product for assessing a risk of developing pressure ulcers, and including one or more computer readable instructions embedded on a tangible, nontransitory computer readable medium and configure to cause one or more computer processors to perform the steps of:

receiving a plurality of patient data with a user input unit, the plurality of patient data for each patient data comprising facility setting information indicative of a location of a patient receiving care and objective and subjective information of said patient for a plurality of categories of said patient data, wherein the facility setting information includes a home facility setting, a hospital facility setting, a nursing home facility setting, a home health care facility setting, and a hospice facility setting, a national database is populated based on the plurality of patient data, including National Database for Nursing Quality Indicators, and a nursing outcomes data registry;

determining with a correlation unit a corresponding risk value of developing a pressure ulcer for each category of the patient data for each patient, based on the patient data received in each category;

adjusting with the correlation unit the corresponding risk value for each category of the patient data for each patient based on the facility setting information, and correlating with the correlation unit the corresponding risk value for each category of the patient data for each patient based on the patient data and facility setting information;

determining with a risk determination unit a level of risk for each patient developing a pressure ulcer based on the correlated risk values of the plurality of categories of the patient data for each patient, the level of risk including a high risk level, a medium risk level, and a low risk level;

measuring with a plurality of sensors, the objective data of a respective patient, that integrate with the risk determination unit to automatically adjust the level of risk of said respective patient based on the correlated risk values of the plurality of categories of the patient data of the respective patient and inputted information from the plurality of sensors;

defaulting with the risk determination unit the level of risk based on the highest correlated risk value of the plurality of categories of the patient data, displaying with a display unit connected to the risk determination unit, based on the plurality of patient data, patient information with color coded indicators corresponding to patients with an active pressure ulcer, and patients with a previous pressure ulcer; and determining and displaying with the risk determination unit, based on the plurality of patient data and the inputted information from the plurality of sensors of the respective patient, a patient safety measurement, and nursing quality information, including a nursing quality measurement, and a nursing performance measurement;

wherein real-time streaming information from sensors is automatically adjusted for re-position reminders for the plurality of patients;

an electronic message system configured for sending reminder messages based on the re-position reminders for the plurality of patients; and wherein the user input unit configured for submitting pressure ulcer risk prevention measures to the nursing outcomes data registry, including a user interface configured to display only when a risk level of a patient is at a predetermined level, an inputted check list from pressure ulcer risk prevention which populates a nursing outcomes data form, an automated documentation tool for nursing staff, which verifies when pressure ulcer prevention tasks are completed, and an automated process between pressure ulcer assessment with data input completion of the nursing outcomes data registries;

a device for real-time measurement of nursing outcomes quality indicators, including a quality measurement device configured to bypasses manual entries, and a quality measurement linked to an individual user or an archived period;

a device for continuously transmitting pressure ulcer risk assessment and education data remotely via the internet to healthcare providers; and a device for integrating pressure ulcer risk level assessment with robotics technology, including a system configured for instructing a robot when re-positioning is due, the robot configured for assistance with the re-positioning, a documentation system configured for documenting when a patient is re-positioned, and an electronic message system configured to send a message to a user regarding the pressure ulcer risk level assessment and the re-positioning.

10. The computer program product of claim 9, further comprising:

displaying with a color-coded visual display risk levels corresponding to the correlated risk values, and including a numerical and word display;

viewing with a multi-user platform the risk levels for allocation of nursing coverage in real time; and tracking with a trend system progress of an individual patient, and accessible from a remote location.

11. The computer program product of claim 9, further comprising:

sorting of the plurality of patients with similar risk levels with a sorting system;

representing by color indicators similar risk levels with the display unit;

providing a display screen or printable sheet of at-risk patients to improve nursing workflow;

allowing for re-positioning in real time with an assessment tool;

sending re-position reminders for a group of patients with a notification device;

displaying at-risk patients simultaneously with a visual screen; and improving continuity of care during shift changes with a visual system.

12. The computer program product of claim 9, further comprising:

indicating information with the display unit and including patients with a particular medical history, including a symbol which indicates a patient with certain medical history, and a visual display of the information in a nursing workflow.

* * * * *